United States Patent
Alaux et al.

(10) Patent No.: US 7,136,714 B2
(45) Date of Patent: Nov. 14, 2006

(54) PROCEDURE FOR DETERMINING MODIFICATIONS MADE TO AN ELECTRONIC CARD AND METHODS OF FABRICATING AN ELECTRONIC CARD AND AN ITEM EQUIPMENT PROVIDED WITH AN ELECTRONIC CARD

(75) Inventors: Philippe Alaux, Buzet sur Tarn (FR); Philippe Pons, Muret (FR)

(73) Assignee: Airbus France, Toulouse (FR)

( * ) Notice: Subject to any disclaimer, the term of this patent is extended or adjusted under 35 U.S.C. 154(b) by 133 days.

(21) Appl. No.: 10/975,834

(22) Filed: Oct. 29, 2004

(65) Prior Publication Data

US 2005/0096773 A1 May 5, 2005

(30) Foreign Application Priority Data

Oct. 30, 2003 (FR) .................................. 03 12723

(51) Int. Cl.
*G06F 19/00* (2006.01)
(52) U.S. Cl. .................. 700/97; 700/95; 382/150; 702/36
(58) Field of Classification Search ............ 700/95–97; 438/16; 382/149–151; 702/36, 35
See application file for complete search history.

(56) References Cited

U.S. PATENT DOCUMENTS

| | | | |
|---|---|---|---|
| 5,598,345 A | 1/1997 | Tokura | |
| 5,764,536 A | 6/1998 | Yamamoto et al. | |
| 6,480,394 B1 | 11/2002 | Feld et al. | |
| 6,990,255 B1 * | 1/2006 | Romanik et al. | 382/284 |
| 2002/0014003 A1 * | 2/2002 | Asai et al. | 29/740 |
| 2003/0174877 A1 * | 9/2003 | Aiger | 382/145 |

FOREIGN PATENT DOCUMENTS

| | | |
|---|---|---|
| CA | 2364564 | 6/2003 |
| DE | 4139189 | 6/1992 |
| EP | 0452905 | 10/1991 |
| EP | 0706027 | 4/1996 |
| EP | 0999440 | 5/2000 |
| FR | 2094751 | 2/1972 |

OTHER PUBLICATIONS

Preliminary Search Report dated Jun. 17, 2004 with English translation.

(Continued)

*Primary Examiner*—Leo Picard
*Assistant Examiner*—Alexander Kosowski
(74) *Attorney, Agent, or Firm*—Stevens, Davis, Miller & Mosher, LLP

(57) ABSTRACT

Procedure for determining modifications made to an electronic card and methods of fabricating an electronic card and an item of equipment provided with an electronic card.

According to the invention, a first diagram (S1) illustrating the electronic card, which includes the electronic components (CE1, CE2, CE3), ports (P1, P2), supply elements (A1) and connection means (L1 to L7) at a first moment is determined, a second diagram illustrating the electronic card at a second moment is determined, a class relating to a change is assigned to each entity in said diagrams, a visual identification attribute is associated with each entity, which is representative of its class, two images corresponding to the first and second diagrams are constructed with the visual identification attributes being displayed, and said images are compared in order to deduce therefrom the modifications made to the electronic card between the first and second moments.

16 Claims, 3 Drawing Sheets

OTHER PUBLICATIONS

M. Moganti, et al.; "Automatic PCB Inspection Algorithms: A Survey," Computer Vision And Image Understanding, Academic Press, US, vol. 63, No. 2, Mar. 1, 1996, pp. 287-313, XP000597539, ISSN: 1077-3142

W.-Y. Wu, et al.; "Automated inspection of printed circuit boards through machine vision", Computers in Industry, Elsevier Science Publishers, Amsterdam, NL, vol. 28, No. 2, May 1, 1996, pp. 103-111, XP004007136, ISSN: 0166-3615.

* cited by examiner

PROCEDURE FOR DETERMINING MODIFICATIONS MADE TO AN ELECTRONIC CARD AND METHODS OF FABRICATING AN ELECTRONIC CARD AND AN ITEM EQUIPMENT PROVIDED WITH AN ELECTRONIC CARD

FIELD OF THE INVENTION

The present invention relates to a procedure for determining modifications made to an electronic card, and also methods of fabricating such an electronic card and an item of equipment provided with such an electronic card, which methods of fabrication use this procedure.

BACKGROUND OF THE RELATED ART

It is known that an electronic card includes constituent elements such as electronic components, ports, supply elements and connection means.

Many items of equipment, both domestic and industrial, comprise one or more electronic cards of this type. Such items of equipment are generally fabricated during a known particular industrial cycle. During this industrial cycle, it is frequently the case that modifications have to be made to the diagram of one or more electronic cards of the item of equipment. These modifications may be involved in several steps of the industrial cycle, especially after tests of a prototype card, during integration into the item of equipment, after tests of a prototype item of equipment, or during changes to the item of equipment in mass production phase.

When modifications have to be made to an electronic card, it is necessary to regenerate industrial data or definition or qualification justification elements, starting from an initial step of acquisition of the diagram illustrating the electronic card. Since the exhaustive testing of an electronic card, and a fortiori an item of equipment that includes at least one such card, is a lengthy and complex operation, the test subsequent to one or more modifications of an electronic card relate in general only to the modified portions of said card. In addition, it is necessary to know how to determine in a precise manner the modifications that have been made to this card since the previous tests.

One solution for determining the modifications made to an electronic card consists in manually noting the modifications as and when an operator modifies the diagram by means of a CAD (Computer-Aided Design) software program. However, this solution has the drawback of there being a not insignificant risk of errors which may in particular be due to omissions by said operator.

Another solution consists in visually comparing the old diagram with the new diagram once the latter has been completed and in noting the differences seen by an operator. Here again, the risk of errors or of omissions is not insignificant, especially if the diagram is complex.

SUMMARY OF THE INVENTION

The object of the present invention is to remedy these drawbacks. It relates to a procedure for easily and reliably determining any modification that has been made between a first moment and a second moment to an electronic card of the aforementioned type.

For this purpose, according to the invention, the procedure is noteworthy in that:

a) a first diagram illustrating said electronic card at said first moment is determined, said first diagram comprising a set of entities representing the below constituent elements (of said electronic card) at said first moment, said first diagram being presented in the form of a first table;

b) a second diagram illustrating said electronic card at said second moment is determined, said second diagram comprising a set of entities representing said constituent elements at said second moment, said second diagram being presented in the form of a second table;

c) a class relating to a change is assigned to each entity in said first and second diagrams;

d) a visual identification attribute is associated with each entity in said first and second diagrams, said visual identification attribute being representative of the class of this entity;

e) first and second images corresponding to said first and second diagrams respectively are constructed, in which the various entities are represented each time with the associated visual identification attribute being displayed; and f) said first and second images are compared in order to deduce therefrom, where applicable, the modifications made to said electronic card between said first and second moments.

Thus, thanks to the invention, it is easily possible to identify, in a visual manner, any modification made to the electronic card by comparing said first and second images, which makes it possible for all the modifications that have been made between said first and second moments to be easily and reliably determined.

Advantageously, at step c), one of the following five classes is assigned to each entity:

an unchanged entity class;

a modified entity class;

a displaced entity class;

an added entity class; and an eliminated entity class.

In a preferred embodiment, at step c), in order to assign a class to each entity in said first and second tables representing said first and second diagrams:

c1) each entity in said first table is considered:

if this entity is not present in said second table, it has been eliminated and said eliminated entity class is assigned thereto;

otherwise:

if the properties of said entity are different in said first and second tables, it has been modified and said modified entity class is assigned thereto; and if the coordinates of said entity are different in said first and second tables, it has been displaced and said displaced entity class is assigned thereto;

c2) each entity in said second table is considered:

if this entity is not present in said first table, it has been added and said added entity class is assigned thereto; and c3) any entity that has not been modified, displaced, added or eliminated is considered as unchanged and said unchanged entity class is assigned thereto.

In a first variant, at step c2), each entity in said second table is considered and a check is made that it is present in said first table.

In a second variant, at step c1), there is associated with each entity present in said first table an indicator in said second table and, at step c2), a search is made in said second table for each entity that is not associated with such an indicator and the added entity class is assigned to each of them.

Furthermore, in a first embodiment, at step c), a class table is formed for each of said classes and, progressively as a class is assigned to the entities, each entity in the class table corresponding to its class is noted.

In a second embodiment, at step c), an additional column corresponding to the class is added to each of said first and second tables and, progressively as a class is assigned to the entities, the name of the class, for each entity, is indicated in said additional column in the row corresponding to this entity in said (first or second) table.

Preferably, each visual identification attribute corresponds to a particular color.

Moreover, advantageously:
- at step e), said first image is constructed in such a way that it includes the unchanged entity, modified entity, displaced entity and eliminated entity classes and said second image is constructed in such a way that it includes the unchanged entity, modified entity, displaced entity and added entity classes; and/or
- at step e), said first and second images are constructed using a computer-aided design tool; and/or
- at step e), a particular visual indication is added to said first and second images when the unchanged entity class has been assigned to all the entities of said first and second images; and/or
- a summary table comprising all the entities of the entity classes other than the unchanged entity class is formed. In this case, a third image representing said summary table is preferably constructed; and/or
- at least one file representative of the determined modifications is formed, which file can be used by a computer-aided design tool.

The present invention also relates to a first method of fabricating at least one electronic card that includes constituent elements comprising electronic components, ports, supply elements and connection means.

Said first method, in which:
- A/ a diagram illustrating said electronic card and comprising a set of entities representing said constituent elements is formed;
- B/ components are positioned and tracks are created on an electrical circuit in order to form a card, in accordance with said diagram;
- C/ the operation of said card is simulated;
- D/ files for fabricating said card are created;
- E/ a prototype card is fabricated using said fabrication files;
- F/ at least one validation test of said prototype card is carried out; and
- G/ at least one electronic card is produced in accordance with said prototype card, is noteworthy according to the invention, in that, when at least one modification is made to said electronic card:
  - α) the aforementioned procedure is implemented in order to determine this modification; and
  - β) said steps B/ to F/ are implemented by carrying out tests only for those parts of said electronic card that are concerned by said modification.

The present invention also relates to a second method of fabricating at least one item of equipment provided with at least one electronic card that comprises constituent elements such as electronic components, ports, supply elements and connection means, in which method:

- O1/ at least one electronic card is fabricated;
- O2/ each electronic card thus fabricated is integrated into a base item of equipment in order to produce a prototype item of equipment;
- O3/ at least one test is carried out on said prototype item of equipment;
- O4/ said prototype item of equipment is validated on the basis of said test; and
- O5/ at least one item of equipment is produced in accordance with said prototype item of equipment.

According to the invention, said second method is noteworthy in that, at step O1/, the aforementioned first method is implemented in order to fabricate at least one electronic card.

Moreover, the present invention also relates to an electronic card and to an item of equipment that are fabricated using said first and second methods presented above, respectively.

BRIEF DESCRIPTION OF THE DRAWING

The figures of the appended drawing will make it clearly understood how the invention can be realized. In these figures, identical references denote similar elements.

DETAILED DESCRIPTION OF THE INVENTION

The subject of the present invention is especially a procedure for determining modifications that are made to an electronic card during its fabrication. Such an electronic card comprises, usually, a board, serving as support and consisting of printed circuits, to which components are soldered.

It is known that an electronic card comprises, in general, as constituent elements:
- active or passive electronic components. An electronic component is passive when it does not require any external supply of power (resistor, capacitor, etc.) and active when it needs an external supply of power (electron tubes, transistor, integrated circuit, etc.);
- ports;
- supply elements (ground, voltage, etc.); and
- connection means.

Figure 1:
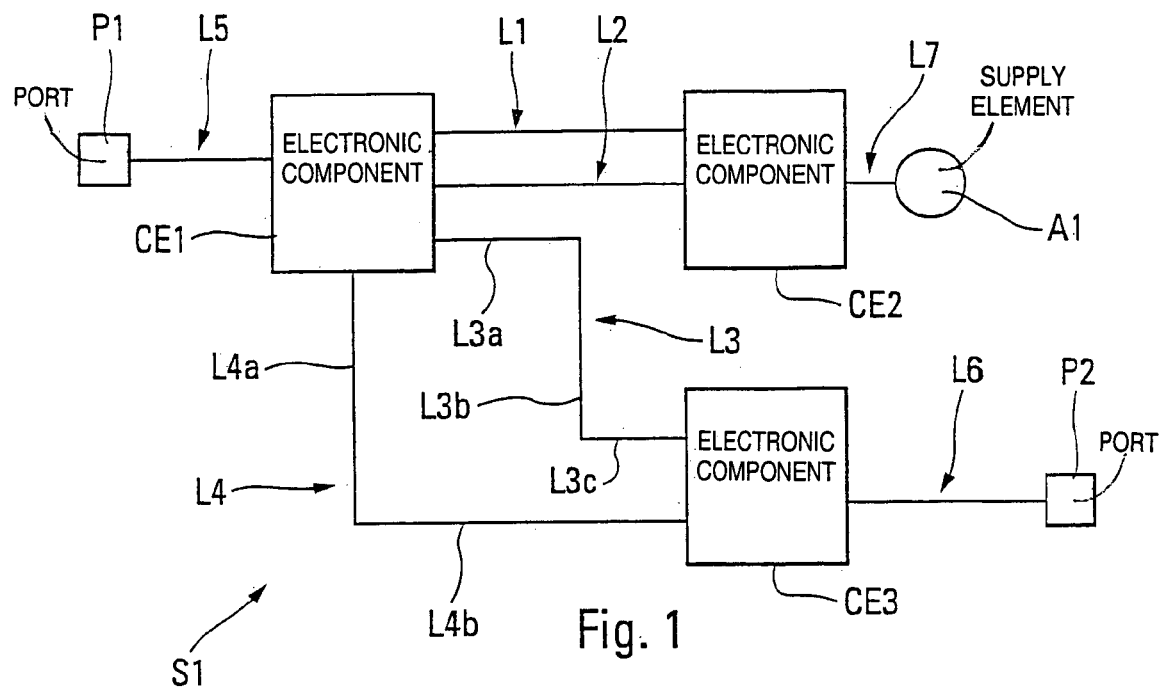
FIG. 1 shows a diagram illustrating an electronic card.

Such an electronic card can be illustrated in the usual manner by a diagram S1, as shown in FIG. 1. Such a diagram consists of one or several sheets. Each sheet comprises a set of entities E1 to E16 representing said constituent elements, namely:
- electronic components CE1, CE2, CE3;
- ports P1, P2 for connecting two connection means together;
- connections means L1 to L7. Each connection means L1 to L7 includes at least one straight segment or link. Thus, the connections means L1, L2, L5, L6 and L7 comprise only a single straight link, whereas the connection means L3 comprises three straight links L3a, L3b and L3c and the connection means L4 comprises two straight links L4a and L4b; and supply elements A1.

In addition, each of said entities E1 to E16 may be characterized by its coordinates in the diagram S1, namely:

by the coordinates of the two end points in the case of a straight link of a connection means; and by the coordinates of a reference point for any entity other than a connection means.

The diagram of an electronic card can therefore be represented in the form of a table, as shown below in the case of said diagram S1 of FIG. 1.

| Entity | Property | Coordinates |
|---|---|---|
| E1 | CE1 | x1, y1 |
| E2 | CE2 | x2, y2 |
| E3 | CE3 | x3, y3 |
| E4 | P1 | x4, y4 |
| E5 | P2 | x5, y5 |
| E6 | L1 | x6a, y6a; x6b, y6b |
| E7 | L2 | x7a, y7a; x7b, y7b |
| E8 | L3a | x8a, y8a; x8b, y8b |
| E9 | L3b | x8b, y8b; x9b, y9b |
| E10 | L3c | x9b, y9b; x10b, y10b |
| E11 | L4a | x11a, y11a; x11b, y11b |
| E12 | L4b | x11b, y11b; x12b, y12b |
| E13 | L5 | x13a, y13a; x13b, y13b |
| E14 | L6 | x14a, y14a; x14b, y14b |
| E15 | L7 | x15a, y15a; x15b, y15b |
| E16 | A1 | x16, y16 |

Figure 2:
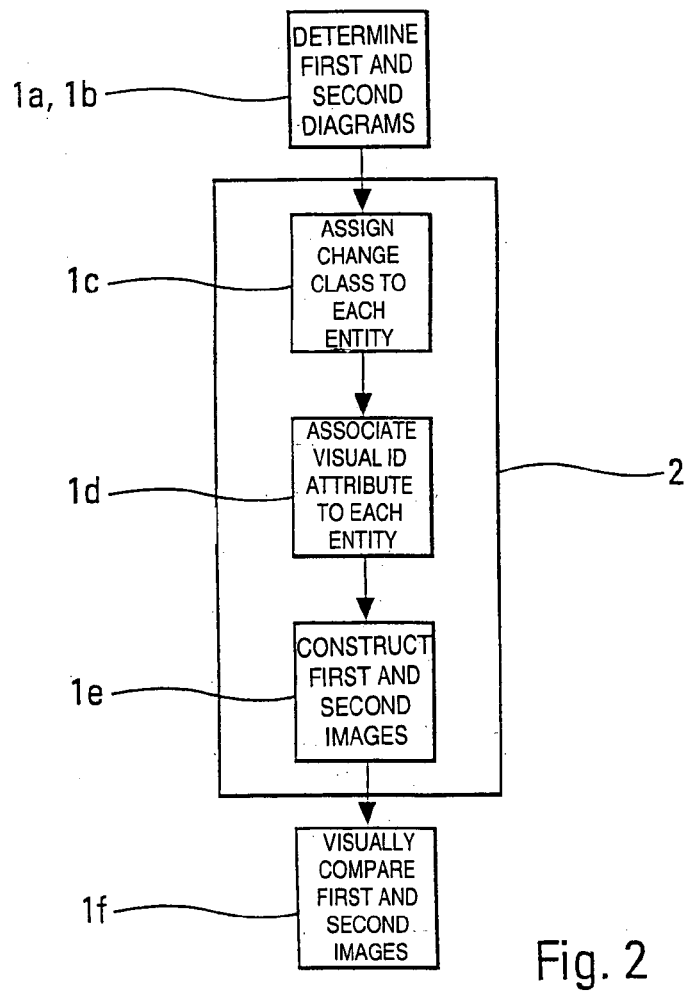
FIG. 2 illustrates the successive steps of a procedure according to the invention.
Figure 3:
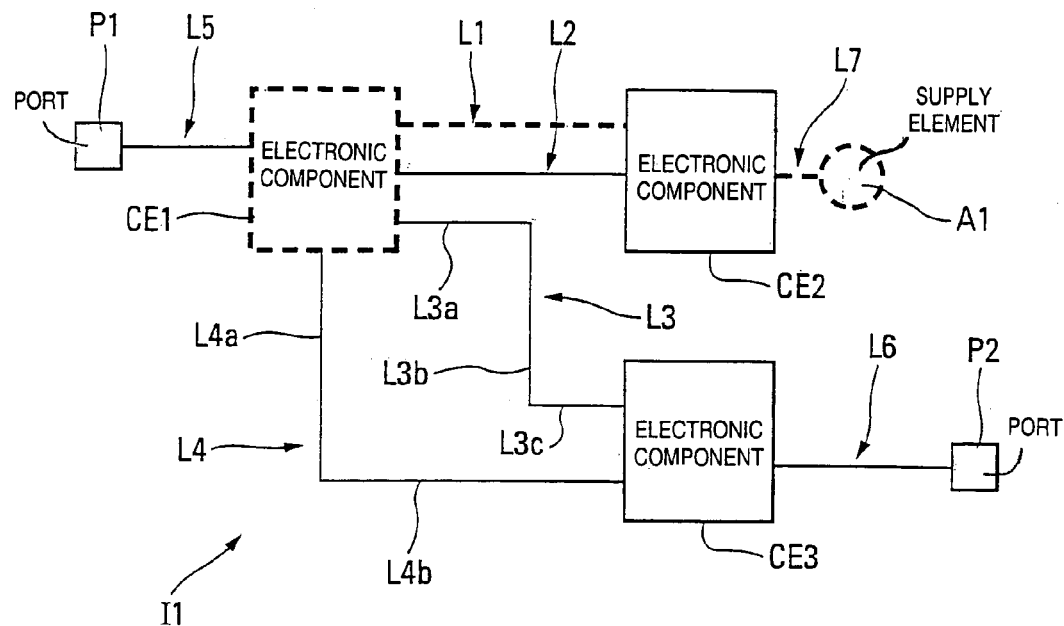
FIGS. 3 and 4 are two images obtained by the invention and showing an electronic card at two different moments.
Figure 4:
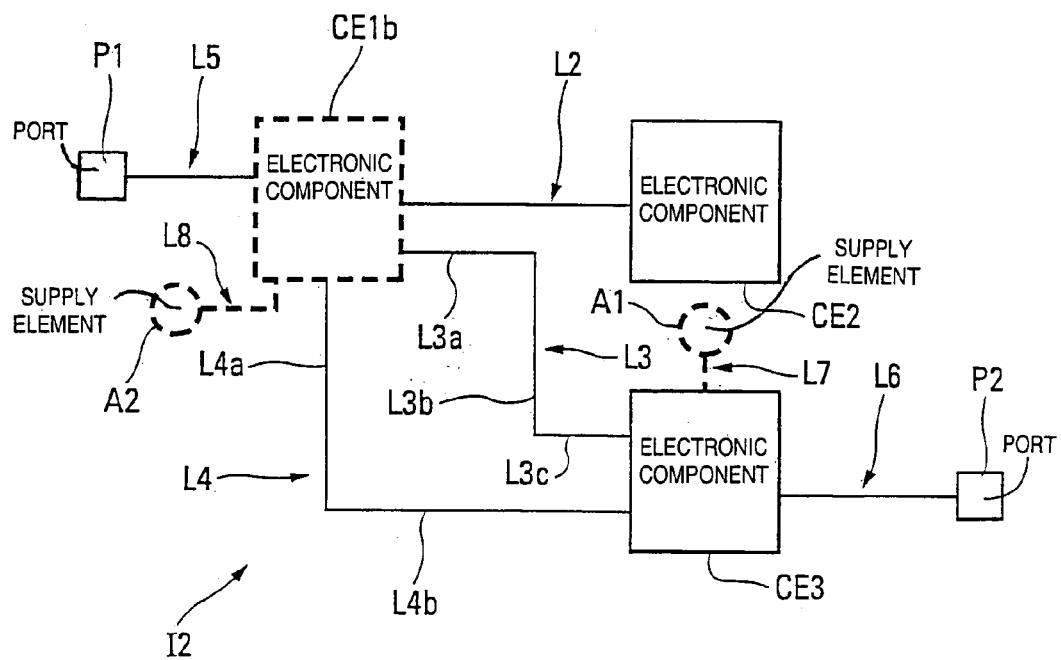

According to the invention, to determine modifications that have been made to such an electronic card between a first moment M1 and a second moment M2 (after said first moment M1), a procedure comprising a series of successive steps 1a to 1f, as illustrated in FIG. 2, is implemented, namely:

Step 1a) for determining a first diagram S1 illustrating said electronic card at said first moment M1, said first diagram comprising a set of entities E1 to E16 representing said constituent elements at said first moment M1, said first diagram being presented in the form of a first table T1 explained below;

Step 1b) for determining a second diagram, illustrating said electronic card at said second moment M2, said second diagram comprising a set of entities E1 to E5 and E7 to E18 representing said constituent elements at said second moment M2, said second diagram being presented in the form of a second table T2 explained below;

Step 1c) for assigning a class relating to a change to each entity in said first and second tables T1 and T2;

Step 1d) for associating a visual identification attribute to each entity in said first and second tables T1 and T2, said visual identification attribute being representative of the class of this entity;

Step 1e) for constructing first and second images I1 and I2 shown in FIGS. 3 and 4 respectively and corresponding to said first and second diagrams respectively, in which the various entities are shown each time with the associated visual identification attribute being displayed; and Step 1f) for comparing (visually) said first and second images I1 and I2 so as to deduce therefrom, where appropriate, the modifications made to said electronic card between said first and second moments M1 and M2.

TABLE T1

| Entity | Property | Coordinates | Class |
|---|---|---|---|
| E1 | CE1 | x1, y1 | M |
| E2 | CE2 | x2, y2 | I |
| E3 | CE3 | x3, y3 | I |
| E4 | P1 | x4, y4 | I |
| E5 | P2 | x5, y5 | I |
| E6 | L1 | x6a, y6a; x6b, y6b | S |
| E7 | L2 | x7a, y7a; x7b, y7b | I |
| E8 | L3a | x8a, y8a; x8b, y8b | I |
| E9 | L3b | x8b, y8b; x9b, y9b | I |
| E10 | L3c | x9b, y9b; x10b, y10b | I |
| E11 | L4a | x11a, y11a; x11b, y11b | I |
| E12 | L4b | x11b, y11b; x12b, y12b | I |
| E13 | L5 | x13a, y13a; x13b, y13b | I |
| E14 | L6 | x14a, y14a; x14b, y14b | I |
| E15 | L7 | x15a, y15a; x15b, y15b | D |
| E16 | A1 | x16, y16 | D |

TABLE T2

| Entity | Property | Coordinates | Class |
|---|---|---|---|
| E1 | CE1b | x1, y1 | M |
| E2 | CE2 | x2, y2 | I |
| E3 | CE3 | x3, y3 | I |
| E4 | P1 | x4, y4 | I |
| E5 | P2 | x5, y5 | I |
| E7 | L2 | x7a, y7a; x7b, y7b | I |
| E8 | L3a | x8a, y8a; x8b, y8b | I |
| E9 | L3b | x8b, y8b; x9b, y9b | I |
| E10 | L3c | x9b, y9b; x10b, y10b | I |
| E11 | L4a | x11a, y11a; x11b, y11b | I |
| E12 | L4b | x11b, y11b; x12b, y12b | I |
| E13 | L5 | x13a, y13a; x13b, y13b | I |
| E14 | L6 | x14a, y14a; x14b, y14b | I |
| E15 | L7 | x15c, y15c; x15d, y15d | D |
| E16 | A1 | x16a, y16a | D |
| E17 | A2 | x17, y17 | A |
| E18 | L8 | x18a, y18a; x18b, y18b | A |

In a first embodiment, and as specified in the above tables T1 and T2, at step 1c) an additional column corresponding to the class is added to each of said tables T1 and T2 and, as a class is progressively assigned to the entities E1 to E18, the name of the class is indicated, for each entity, in said additional column, in the row corresponding to this entity in said table T2 or T2.

More precisely, one of the following five classes is assigned to each entity E1 to E18:

an unchanged entity class I;

a modified entity class M;

a displaced entity class D;

an added entity class A; and an eliminated entity class S.

In a second embodiment, at step 1c, a class table is formed for each of said classes I, M, D, A and S and, progressively as a class is assigned to said entities E1 to E18, each entity in the class table corresponding to its class is noted.

According to the invention, at step 1c, to assign a class to each entity E1 to E18 in said tables T1 and T2 representing said first and second diagrams:

c1) each entity in said table T1 is considered:

if this entity is not present in said table T2, such as the entity E6 for example, it has been eliminated and said eliminated entity class S is assigned thereto;

otherwise:

if the properties of said entity are different in said tables T1 and T2, as in the case of the entity E1 for example, it has been modified and said modified entity class M is assigned thereto; and if the coordinates of said entity are different in tables T1 and T2, as in the case of the entities E15 and E16 for example, it has been displaced and said displaced entity class D is assigned thereto;

c2) then, each entity in said table T2 is considered:

if this entity is not present in said table T1, such as the entities E17 and E18 for example, it has been added and said added entity class A is assigned thereto; and c3) any entity that has not been modified, displaced, added or eliminated is considered as unchanged, like the entities E2 and E3 for example, and said unchanged entity class I is assigned thereto.

With regard to said added entity class A:

in a first variant, at step c2, each entity in said table T2 is considered and a check is made that it is present in said table T1; and in a second variant, at step c1, there is associated with each entity present in said table T1 an indicator representative of this presence in said table T2 and, at step c2, a search is made in said table T2 for each entity that has not been associated with such an indicator and the added entity class A is assigned to each of them.

In a preferred embodiment, the visual identification attribute associated with each entity E1 to E18 corresponds to a color in which this entity is shown in the corresponding image I1, I2. For example, the unchanged entities may be shown in black, the modified entities in blue, the displaced entities in yellow, the eliminated entities in red and the added entities in green.

Advantageously, said first and second images I1 and I2 are constructed by means of a CAD (Computer-Aided Design) software program used for inputting the diagrams in question. The computer-aided design comprises, in general, all the computing techniques serving to create data describing an object to be designed, to manipulate this data, for the purpose of ending up with a completed design shape, and to generate information needed to fabricate this object. To do this, at step 1d, the files corresponding to these diagrams are modified so as to assign a color to each entity depending on the class to which it belongs. At step 1e, the files thus modified are then displayed (by means of said CAD software) on an associated suitable display means. Preferably, to keep the files corresponding to the diagrams intact, these modifications are made on copies of said files.

In a preferred embodiment, when all the entities in tables T1 and T2 are of the unchanged entity class I, at step 1e a visual indication is added to said images I1 and I2 in order to indicate that the two compared diagrams are identical. For example, a label "UNCHANGED" may be displayed in capitals in the background of each of said images I1 and I2.

In one particular embodiment, a summary table comprising all the entities of classes M, D, A, S other than the unchanged entity class I is formed. In this case, a third image (not shown) corresponding to said summary table is constructed.

The invention therefore has the advantage of making it easy for the modifications made to an electronic card to be visually identified, by visually comparing said images I1 and I2. In FIGS. 3 and 4, the modifications made are displayed by bold broken lines, for the purpose of simplifying the drawing. In practice, this display is preferably achieved by a set of various colors, as indicated above.

In addition, one or more files representative of the modifications made to the electronic card are constructed, these files being capable of being used by CAD tools during steps of an industrial fabrication cycle (or method) explained below, so as to determine the tests that have to be carried out subsequent to said modifications.

It should be noted that steps 1c to 1e may be grouped together into a single step 2, which may be implemented automatically by suitable software, created especially for this purpose.

The aforementioned procedure according to the invention has been described in the case of a sheet of a diagram. Of course, it applies in the same manner to each sheet of a diagram comprising several sheets and, in this case, the abovementioned sheet(s) may relate in general to all of the sheets of the diagram.

The procedure according to the present invention may be used to compare two diagrams of an electronic card corresponding to consecutive versions of the same diagram (for example version N and version N+1). However, this use should not be envisioned as being limiting, and said procedure can thus also be used to compare diagrams corresponding to non-consecutive versions of the same diagram (for example version N and version N+k, where k>1).

Figure 5:
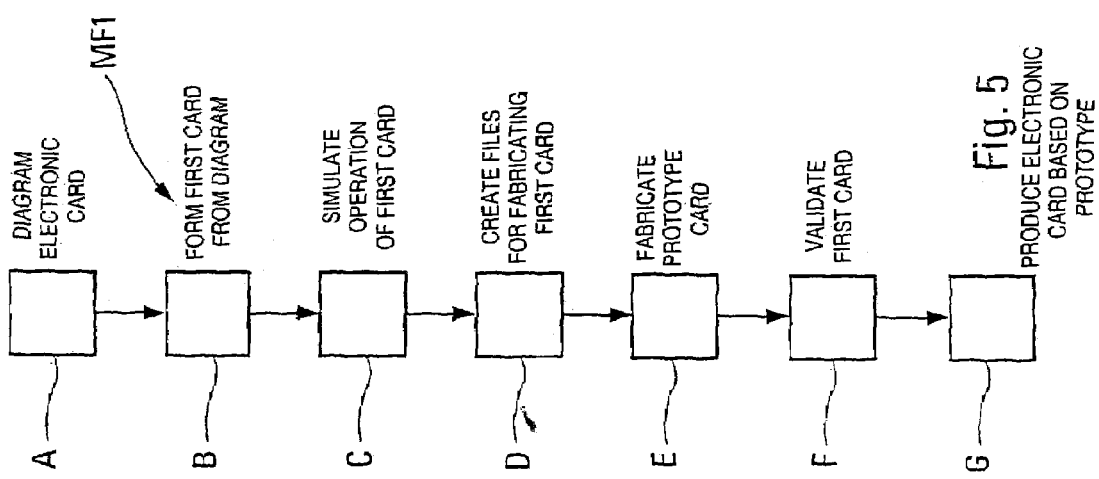
FIG. 5 illustrates the successive steps of a method of fabricating, according to the invention, an electronic card.

The present invention also relates to a method MF1 of fabricating at least one electronic card of the aforementioned type. This method MF1 comprises steps A to G, shown in FIG. 5 and consisting in:

A/ forming a diagram illustrating said electronic card and comprising a set of entities E1 to E16 representing the constituent elements of said electronic card;

B/ positioning components and creating tracks on an electrical circuit in order to form a first card, in accordance with said diagram;

C/ simulating the operation of said first card;

D/ creating files for fabricating said first card.

E/ fabricating, using said fabrication files, a prototype card, i.e. a first example that is constructed by industrial-scale means and is intended for tests with a view to mass production;

F/ carrying out at least one test for validating said prototype card; and

G/ producing at least one electronic card in accordance with said prototype card. In general, such a production line is, of course, a mass production run.

According to the invention, when at least one modification is made to said electronic card during its fabrication:

α) the aforementioned procedure (steps 1a to 1f) is implemented in order to determine this modification; and β) said steps B/ to F/ are implemented by carrying out tests only for those portions of said electronic card that are concerned by the modification(s) thus determined.

Figure 6:
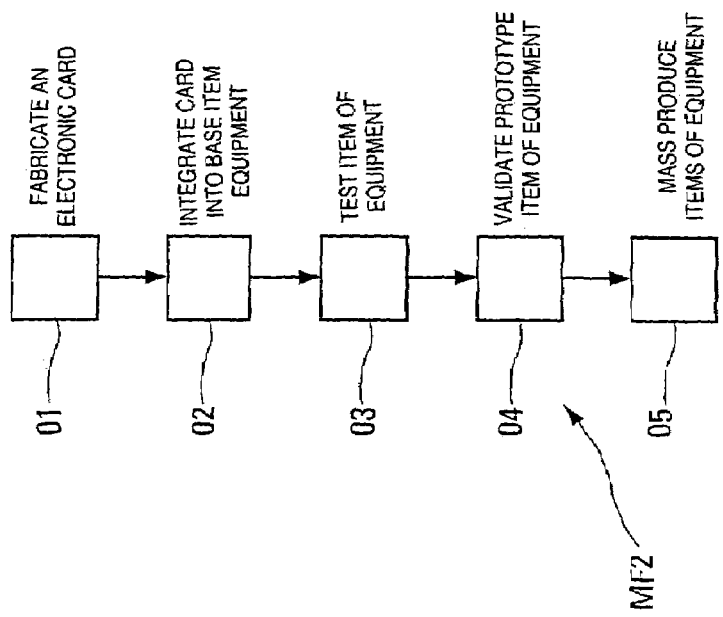
FIG. 6 illustrates the successive steps of a method of fabricating, according to the invention, an item of equipment provided with an electronic card.

The present invention also relates to a method MF2 of fabricating at least one item of equipment provided with at least electronic card of the aforementioned type. This method MF2 comprises steps O1 to O5, shown in FIG. 6 and consisting in:

O1/ fabricating at least one electronic card using said method MF1 presented above;

O2/ integrating each electronic card thus fabricated into a base item of equipment in order to produce a prototype item of equipment;

O3/ carrying out at least one test on said prototype item of equipment;

O4/ validating said prototype item of equipment on the basis of said test; and

O5/ mass producing items of equipment in accordance with said prototype item of equipment.

The invention claimed is:

1. A procedure for determining modifications made to an electronic card having constituent elements comprising electronic components, ports, supply elements and connection components, between a first moment and a second, subsequent moment, wherein:
   a) a first diagram illustrating said electronic card at said first moment is determined, said first diagram comprising a set of entities representing said constituent elements at said first moment, said first diagram being presented in the form of a first table;
   b) a second diagram illustrating said electronic card at said second moment is determined, said second diagram comprising a set of entities representing said constituent elements at said second moment, said second diagram being presented in the form of a second table;
   c) a class relating to a change is assigned to each entity in said first and second tables representing said first and second diagrams, as follows:
      c1) each entity in said first table is considered:
         if this entity is not present in said second table, it has been eliminated and an eliminated entity class is assigned thereto;
         otherwise:
            if the properties of said entity are different in said first and second tables, it has been modified and a modified entity class is assigned thereto; and
            if the coordinates of said entity are different in said first and second tables, it has been displaced and a displaced entity class is assigned thereto;
      c2) each entity in said second table is considered:
         if this entity is not present in said first table, it has been added and an added entity class is assigned thereto; and
      c3) any entity that has not been modified, displaced, added or eliminated is considered as unchanged and an unchanged entity class is assigned thereto;
   d) a visual identification attribute is associated with each entity in said first and second diagrams, said visual identification attribute being representative of the class of this entity;
   e) first and second images corresponding to said first and second diagrams respectively are constructed, in which the various entities are represented each time with the associated visual identification attribute being displayed; and
   f) said first and second images are compared in order to deduce therefrom, where applicable, the modifications made to said electronic card between said first and second moments.

2. The procedure as claimed in claim 1, wherein, at step c2), each entity in said second table is considered and a check is made that it is present in said first table.

3. The procedure as claimed in claim 1, wherein, at step c1), there is associated with each entity present in said first table an indicator in said second table and, at step c2), a search is made in said second table for each entity that is not associated with such an indicator and the added entity class is assigned to each of them.

4. The procedure as claimed in claim 1, wherein, at step c), a class table is formed for each of said classes and, progressively as a class is assigned to the entities, each entity in the class table corresponding to its class is noted.

5. The procedure as claimed in claim 1, wherein, at step c), an additional column corresponding to the class is added to each of said first and second tables and, progressively as a class is assigned to the entities, the name of the class, for each entity, is indicated in said additional column in the row corresponding to this entity in said table.

6. The procedure as claimed in claim 1, wherein each visual identification attribute corresponds to a particular color.

7. The procedure as claimed in claim 1, wherein, at step e), said first image is constructed in such a way that it includes the unchanged entity, modified entity, displaced entity and eliminated entity classes and said second image is constructed in such a way that it includes the unchanged entity, modified entity, displaced entity and added entity classes.

8. The procedure as claimed in claim 1, wherein, at step e), said first and second images are constructed using a computer-aided design tool.

9. The procedure as claimed in claim 1, wherein, at step e), a particular visual indication is added to said first and second images when the unchanged entity class has been assigned to all the entities of said first and second images.

10. The procedure as claimed in claim 1, wherein a summary table comprising all the entities of the entity classes other than an unchanged entity class is formed.

11. The procedure as claimed in claim 10, wherein a third image representing said summary table is constructed.

12. The procedure as claimed in claim 1, wherein at least one file representative of the determined modifications is formed, which file can be used by a computer-aided design tool.

13. A method of fabricating at least one electronic card comprising constituent elements comprising electronic components, ports, supply elements and connection components, in which method:
   A/ a diagram illustrating said electronic card and comprising a set of entities representing said constituent elements is formed;
   B/ components are positioned and tracks are created on an electrical circuit in order to form a card, in accordance with said diagram;
   C/ the operation of said card is simulated;
   D/ files for fabricating said card are created;
   E/ a prototype card is fabricated using said fabrication files;
   F/ at least one validation test of said prototype card is carried out; and
   G/ at least one electronic card is produced in accordance with said prototype card, wherein, when at least one modification is made to said electronic card:
      α) the procedure specified in claim 1 is implemented in order to determine this modification; and
      β) said steps B/ to F/ are implemented by carrying out tests only for those parts of said electronic card that are concerned by said modification.

14. An electronic card having constituent elements comprising electronic components, ports, supply elements and connection components, which card is fabricated by implementing the method of fabrication specified in claim 13.

15. A method of fabricating at least one item of equipment provided with at least one electronic card that comprises constituent elements comprising electronic components, ports, supply elements and connection components, in which method:

O1/ at least one electronic card is fabricated;

O2/ each electronic card thus fabricated is integrated into a base item of equipment in order to produce a prototype item of equipment;

O3/ at least one test is carried out on said prototype item of equipment;

O4/ said prototype item of equipment is validated on the basis of said test; and O5/ at least one item of equipment is produced in accordance with said prototype item of equipment, wherein, at step O1/, the method of fabrication specified in claim 13 is implemented in order to fabricate at least one electronic card.

16. Item of equipment provided with at least one electronic card that has constituent elements comprising electronic components, ports, supply elements and connection components, which is fabricated by implementing the method of fabrication specified in claim 15.

\* \* \* \* \*